United States Patent [19]

Filler et al.

[11] Patent Number: 5,554,498
[45] Date of Patent: Sep. 10, 1996

[54] NUCLEIC ACID AMPLIFICATION USING SCANDIUM AND LANTHANUM IONS

[75] Inventors: Aaron G. Filler, Seattle, Wash.; Andrew M. L. Lever, Cambridge, England

[73] Assignee: Syngenix Limited, Cambridge, United Kingdom

[21] Appl. No.: 204,144

[22] PCT Filed: Sep. 1, 1992

[86] PCT No.: PCT/GB92/01599

§ 371 Date: Feb. 28, 1994

§ 102(e) Date: Feb. 28, 1994

[87] PCT Pub. No.: WO93/05174

PCT Pub. Date: Mar. 18, 1993

[30] Foreign Application Priority Data

Aug. 30, 1991 [GB] United Kingdom ............ 9118676
Nov. 7, 1991 [GB] United Kingdom ............ 9123677
Mar. 13, 1992 [GB] United Kingdom ............ 9205470
Mar. 24, 1992 [GB] United Kingdom ............ 9206402

[51] Int. Cl.$^6$ .......................... C12P 19/34; C12Q 1/00; C12Q 1/68; C12Q 1/70
[52] U.S. Cl. ............................. 435/5; 435/6; 435/91.2; 435/810
[58] Field of Search ...................... 435/5, 6, 91.2, 435/810; 935/77, 78

[56] References Cited

FOREIGN PATENT DOCUMENTS 0386857  9/1990  European Pat. Off. .

OTHER PUBLICATIONS

Erlich A. Henry, "PCR Technology—Principles and Applications for DNA Amplification," Published 1990 by Stockton Press (U.S.), pp. 1–22.

Sarkander, H.–I., C. G. Uthoff (1978) "Modification of RNA Synthesis in Isolated Rat Liver Nuclei during Anticoagulant Treatment with Lanthanides" Arzneimittel Forschung 28(1):21–24.

*Primary Examiner*—Stephanie W. Zitomer
*Assistant Examiner*—Paul B. Tran
*Attorney, Agent, or Firm*—Saliwanchik & Saliwanchik

[57] ABSTRACT

The subject invention pertains to a method for amplifying the polymerase activity of a nucleic acid polymerase using Group 3 ions. Group 3 ions of the subject invention can also be used to inhibit the enzymatic activity of nucleases. The subject invention further concerns a method for identifying an unknown nucleic acid polymerase or other enzymes in a sample.

9 Claims, 1 Drawing Sheet

NUCLEIC ACID AMPLIFICATION USING SCANDIUM AND LANTHANUM IONS

This application is a 371 of PCT/GB92/01599, filed Sep. 1, 1992.

BACKGROUND OF THE INVENTION

This invention concerns a new class of reagents for use in the field of molecular biology and related areas of biochemistry. The wide and general usefulness of these reagents is based upon the widespread role of the divalent cations, magnesium ($Mg^{2+}$) and calcium ($Ca^{2+}$) in reactions involving nucleic acids. The magnesium cation in particular affects the annealing pattern of nucleic acid strands, the secondary and tertiary structure of DNA, RNA or RNA/DNA strands, and the properties of nucleotides which universally tend to complex with divalent cations.

In addition, divalent cations are of great importance in moderating the function of a wide range of nuclease enzymes which digest nucleic acid strands into their component monomeric nucleotides and nucleosides and are also important in the function of DNA and RNA polymerase enzymes which assemble DNA and RNA strands from their component nucleotides. The rate of function of nucleic acid polymerases, the processivity (tendency to continue forward reactions along a template strand), the accuracy, and the tolerance for improper or abnormal base sequences or substitute nucleotides are all well known to be affected by variations in the concentration of magnesium in the reaction medium.

It has been known for a number of years that various other divalent cations, most particularly manganese, could substitute for magnesium and essentially replicate its effects though often at somewhat lower concentrations. However, since magnesium is a convenient and inexpensive reagent, and since none of these cation substitutions achieved any biochemically novel or helpful additional result, there has been no industrial application of such substitutions. Further, many divalent cations of transition metals cannot tolerate the thioprotectants and reductants such as β-mercaptoethanol and dithiothreitol (DTT) which are required by several of the polymerase enzymes for proper function, since these reductants tend to reduce and precipitate the transition metal cations.

BRIEF SUMMARY OF THE INVENTION

The subject invention concerns a method for amplifying the polymerase activity of a nucleic acid polymerase using Group 3 ions. Advantageously, the Group 3 ions of the subject invention can be used to inhibit the activity of nucleases or other enzymes that may be present in a sample. Specifically exemplified are the Group 3 ions scandium and lanthanum. The subject invention further concerns a method for identifying an unknown nucleic acid polymerase or other enzymes in a sample.

DETAILED DESCRIPTION OF THE INVENTION

Figure 1:
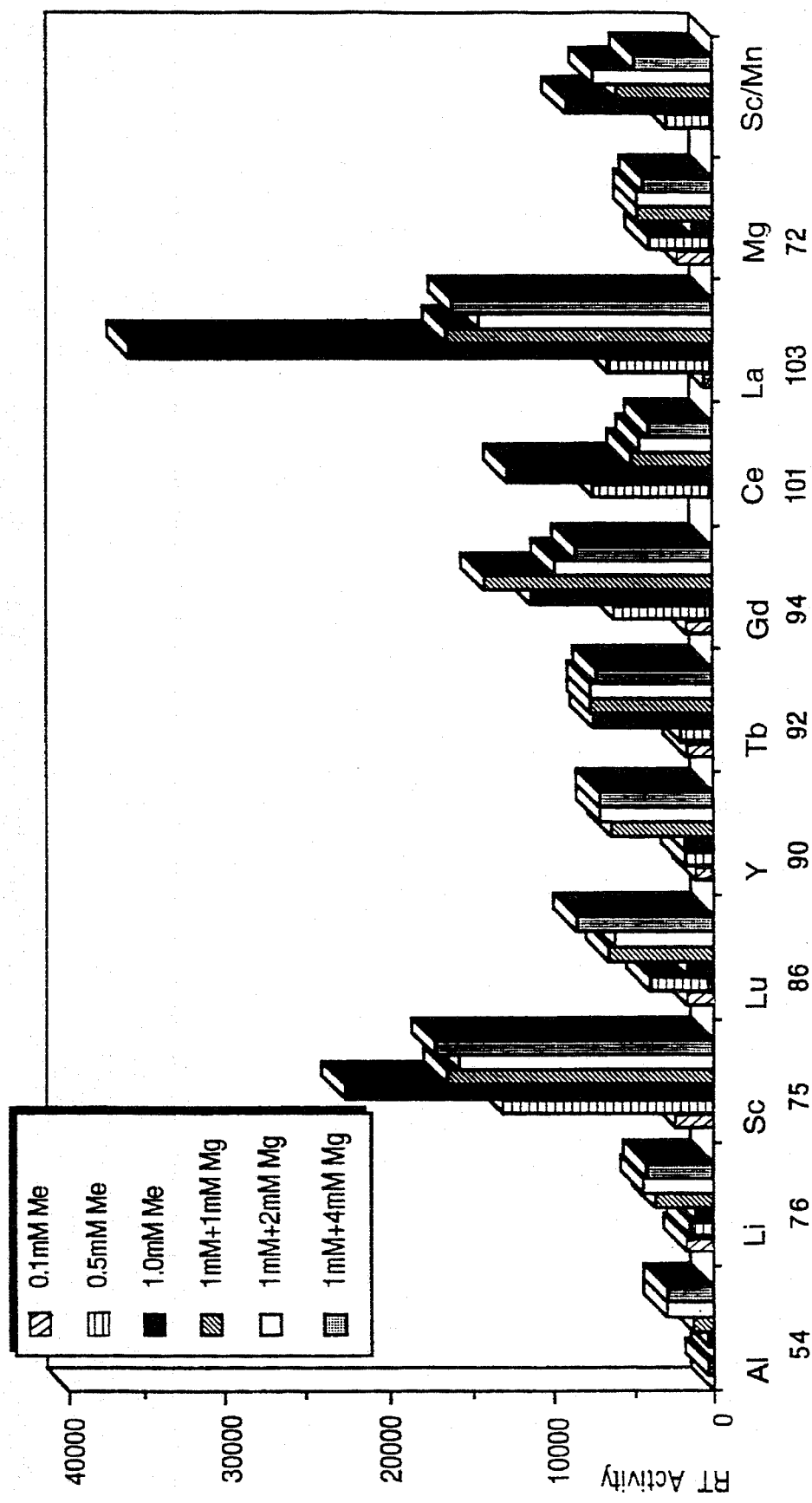
FIG. 1 shows the polymerase activity of reverse transcriptase (RT) when treated with various cations.

The inventors have very surprisingly discovered, however, that when certain obscuring factors are controlled for, and when several less common cations, particularly trivalent cations are used in place of magnesium or calcium or in mixtures with them, that several novel and very useful effects can be achieved. It is helpful that these cations are not reduced by DTT or β-mercaptoethanol. It has been known that some such trivalent cations could substitute for e.g. calcium in some enzymes and cause an enzyme inhibition effect. It has been demonstrated by the inventors that it is possible to inhibit nuclease enzymes in this way.

Most importantly, however, the inventors have made the surprising scientific discovery that many trivalent cations can actually increase the processivity of some nucleic acid polymerase enzymes. In the case of the reverse transcriptase enzyme which is used by some pathogenic retroviruses such as the HIV virus which causes AIDS, it is possible to increase the rate of DNA production and to increase the average length of the DNA copies of RNA templates made by the enzyme. This is most important when one wishes to assay a sample of potentially infected human blood to see if it contains any viral reverse transcriptase enzyme capable of e.g. producing DNA upon an RNA template and so learn if that persons has HIV infection of the blood.

Use of the appropriate trivalent cation in place of magnesium in the reaction therefore has a double useful effect. At the same time, it inhibits the nucleases which normally tend to destroy the products of the reverse transcriptase (RT) reaction and stimulates the processivity, hence the rate of production of the viral DNA. Thus, with magnesium as the divalent cation, the DNA which is slowly produced is often destroyed by nucleases and so cannot be detected. Thus, an assay fails to detect infection until the RT is present in relatively large amounts. However, using appropriate cation substitution, the diagnostically important DNA is produced at a faster rate and is less likely to be destroyed by nucleases thus increasing the diagnostic product and hence the sensitivity of the assay in two synergistic ways.

The manipulation of nucleic acid annealing, priming and folding of secondary or tertiary structure is also of very great importance in the field of use of the polymerase chain reaction (PCR) which is of enormous industrial importance in all areas of molecular biology. The use of substitute cations or mixtures of cations with appropriate chelators can be used to manipulate several aspects of the PCR reaction.

In PCR, the crux of the reaction involves a nucleic acid polymerase such as Taq polymerase (from Thermophilus aquaticus) which is functional at high temperatures such as 72° C. or a polymerase such as the T4 DNA polymerase which can only be used at lower temperatures but is more accurate. To make a large number of copies of a single DNA strand, a small amount of Taq is put in a reaction well with the DNA strand, monomeric nucleotides, and primer strands 30–50 base pairs in length which have some complementarity to the DNA of interest.

The mixture is taken through a three step cycle in which it is heated to 92° C. to denature the DNA into its separate single strands, then cooled to 55° C. to permit annealing of template to primer, then brought to 72° C. to permit Taq to extend the primer to copy the template. The two resulting DNA strands are then taken through the same cycle yielding four copies, and so on, until after about 20 cycles there are a million copies and the reaction begins to plateau.

The plateau occurs because the small amount of Taq polymerase added at the outset becomes unable to rapidly copy all the million or so strands. It also occurs because there are so many single strands, that many strands anneal to other single strands rather than to primer thus limiting the amount of exposed template for Taq to work upon.

Cation substitution with trivalents (e.g. Scandium, Yttrium, and elements of the lanthanide series) or substitution with useful divalents (Mn, Pd, Co, Cu, Sr) can affect PCR in several ways. The plateau can be elevated and hence the yield increased by increasing the rate and processivity of the Taq or T4 DNA polymerase so that it is less easily overwhelmed by the total number of templates to copy. It is also possible to affect the tendency of the single strands to anneal in preference to the primers and so again the plateau may be affected.

An additional benefit from increasing processivity is the ability to work with longer templates, since the polymerase will be more likely to complete a full copy of the template. Manipulation of the accuracy of transcription is also possible, since in some situations, the most accurate possible transcript is sought, while in others, it is important to insure that altered primers can be used to add desired sequences to the final product DNA.

Effects upon primer and strand annealing are also important where it is desired to use shorter primers (e.g. 12–15 bp) at high temperatures, or to permit annealing at 72° C. to avoid the third step of the cycle. Other important phenomena in PCR which are susceptible to cation effects are the noise due to primer-dimer contamination and to "non-template directed" primer extension. Alterations in annealing stringency are important both for purposely introducing modified sequences on the primer and also in the fundamental selectivity and specificity of the reaction for the DNA of interest as demonstrated by the ability to produce a single relatively homogenous band upon gel electrophoresis analysis of the product.

In addition to uses in RT assays and in PCR, these reagents may also be used in a wide variety of other useful reactions in molecular biology and biochemistry in which nucleases, polymerases, and primer/template interactions figure prominently. These include DNA syntheses, genetic modifications, gene therapies, gene insertions or other genetic tests, cloning reactions, assembling vectors, priming, nick translation, labelling of strands and a wide variety of other reactions.

The unique feature of these reagents is the previously unknown use of certain lanthanide or other related elements or similarly acting small molecules which have in common the special ability to inhibit certain intracellular enzymes called nucleases and some of which also have the ability to improve the processivity (e.g. stimulate the activity) of certain nucleic acid polymerases such as the reverse transcriptase enzyme of HIV.

The physician or laboratory chemist is often faced with the problem of testing a sample of blood or other tissue for the presence of the Human Immunodeficiency Virus. There are currently two widely used schemes for carrying out such tests. One such scheme involves using antibodies to detect the presence of a typical protein of HIV called p24. These assays require expensive specialised antibody reagents and are subject to loss of efficacy when mutations occur to produce new strains of HIV whose p24 protein may not be recognised by the antibody reagent in use.

An alternate approach to detecting HIV is potentially far more specific, sensitive, and immune to alteration by mutation, but this full potential has proven difficult to exploit. This method involves use of the reverse transcriptase (RT) enzyme of the virus. The RT enzyme has three important functions and the very existence of the virus depends upon them. This is why a mutation which destroys any of these functions renders the virus nonviable.

Several molecules of the RT enzyme are included in the nucleocapsid of the virus along with two copies of the genome of the virus which is encoded in special strands of RNA. Upon penetration of a human cell, the RT enzyme is activated and gradually makes a single strand cDNA copy of the RNA strand ("RNA-dependent DNA polymerase"). Next, an "RNase H" function of the RT enzyme digests away the original RNA template strand. Finally, a "DNA-dependent DNA polymerase" function makes a complementary DNA strand to produce the final double stranded DNA copy of the viral genome which can be inserted into the DNA genetic material of the human cell whenever the human cell next starts to replicate.

A number of well known assays have been developed which detect the very unique "RNA-dependent DNA polymerase" function of the RT enzyme a good example of which is reported by Potts (in "Techniques in HIV Research"; eds. Aldovini, A, and Walker, B. D.; pp.103–106, Stockton Press, N.Y. 1990). While these are widely used, they have not been as sensitive as the p24 assay at detecting low levels of infection. Indeed many reports indicate that the p24 ELISA assay is 10 to 100 times more sensitive than the RT based assays.

The ELISA technique is 99% accurate, however, since only 25 HIV positive individuals may be found among 10,000 clinical samples screened, there can be 100 false positive results from such a group. This may mean four incorrect results for every correct one, all of which must then be screened by a second method. There is also a poor correlation between serum p24 antigen level and the amount of infectious virus in the blood of ill patients. Highly sensitive polymerase chain reaction (PCR) techniques have been advocated for this second step. However, the ELISA technique also risks false negatives which might be detected only by a second fast, inexpensive screening technique for which RT assay would be much better suited than PCR.

A second reason for interest in developing sensitive RT assays is that the reverse transcriptase enzyme is the target for the only existing medications for AIDS and there is currently a large scale effort underway to screen tens of thousands of compounds in order to discover new and specific reverse transcriptase inhibitors as well as a vast effort to screen various combinations of these agents in order to develop new therapies for the treatment of HIV infected patients.

A set of limitations applying to RT assays in drug screening efforts concerns the considerable variability in the relation between measured RT activity and the actual infectivity or the number of viral particles present. These variations are due to the presence of various nucleases and other inhibiting substances in some cell lines or patient sera. It is precisely these limitations, as well as the problems of low sensitivity which are addressed by the invention described in this application.

Under purely in vitro conditions with purified enzymes and carefully selected cofactors, the RT enzyme assay is exceedingly sensitive to small amounts of the enzyme. However, the sensitivity is greatly reduced when the assay is performed on the "cell free supernatants" or blood sera of infected humans. The causes for this loss of sensitivity have not been completely clear and it has been considered that there are various cross reactions and contaminants in the complex biochemical setting of plasma or cell free culture supernatants.

There has been some suggestion that there might exist some nuclease enzymes which could digest or destroy the DNA or the RNA template and so work in opposition to the RT enzyme. If the nuclease was exceedingly efficient, it might destroy all of the DNA produced by the RT as fast as it was produced. Under these conditions, the assay would erroneously fail to detect the presence of the virus in a sample. Normally, however, the nuclease might cause a relative decrease in the amount of DNA produced, but the amount of this decrease has never been known.

The basic idea of the assay is to provide templates of polyAdenosine RNA with an oligo $dT_{(8-12)}$ primer DNA, add KCl, $MgCl_2$, Dithiothreitol, pH 8.0 buffers such as Tris, and a detergent such as NP-40 to rupture the virus and expose the enclosed RT enzymes. When $^{32}P$ radiolabelled dTTP (deoxy thymidine triphosphate) is added, the RT enzyme commences making $^{32}P$ labelled single strand polydT DNA upon the RNA template. After 90 minutes, a sample of the reaction product is dotted onto DE81 Whatman paper upon which the DNA adheres to the paper. Unincoporated $^{32}P$ dTTP is washed away and the paper then β-counted to determine the amount of DNA produced on the RNA template, or exposed by autoradiography for a preliminary estimation.

It should be noted that the method described in this application can be used with nucleotides labelled with $^{32}P$, $^{3}H$, $^{35}S$, or various other radiolabels. In addition, it is possible to use nucleotides labelled with brdU (5-bromo2'-deoxyuridine triphosphate) or with digoxigenin. The inventors have carried out RT reactions for assay with nonradioactive nucleotide label for immunoreagent detection.

It is also noted that since some lanthanides such as Scandium have been shown by the inventors to increase the processivity of the RT enzyme. The enzyme normally produces numerous small fragments of DNA broken at characteristic points depending upon the secondary or tertiary structure of the RNA template. In the presence of various lanthanides at 1 mM, or in a metal buffering reagent with a low affinity chelator such as nitrilotriacetic acid, particularly when no divalent cation is provided, then the RT enzyme produces more DNA transcripts in a given amount of time and these transcripts are, on the average, longer than those resulting from the reaction in the presence of a divalent cation such as $Mg^{2+}$ (see FIG. 1).

Because of this direct effect upon processivity, independent of any additional effect gained by inhibiting nucleases, it is possible to use these lanthanide acceleration reagents even when purified, bacterially cloned RT enzyme is used. Further, this processivity effect means that the lanthanide reagents are also quite useful even when the RT enzyme is isolated out of cell culture supernatants or sera by means of immobilised anti-RT antibodies as described by Porstmann et al (J. Virol. Meth. 31:181–188, 1991).

It has now been discovered that, when ions of a Group 3 (IUPAC) element, e.g. Sc, Y or a lanthanide, especially lanthanum or scandium, are present in the reaction mixture then the rate of production of the cDNA by reverse transcriptase can be increased up to 500%. Further, the assay is made sensitive to far smaller amounts of the enzyme. It is well known that lanthanum can inhibit calcium-dependent enzymes. It is also known that many nucleases are dependent on calcium for their activity. Thus by introducing, say, lanthanum or some other nuclease inhibitor into the reaction mixture, the nuclease is blocked, and the recovery of freshly synthesised cDNA on the DE81 paper is dramatically increased.

The most dramatic enhancing effect of the lanthanum may not be seen in assays of purified enzyme because there are typically no nucleases present in the highly purified preparations. Some enhancing effect may still be seen, because of the effect on processivity. However, these enzymes are variably present in cell-free supernatants and plasma. Therefore, in order to improve the uniformity, comparability, and sensitivity of reverse transcriptase assays, a novel reaction buffer mixture or "cocktail" is prepared. These anti-nuclease cocktails can be used in a wide range of other assays or gene insertion tasks where it is important to protect DNA or RNA from digestion by nuclease enzymes in the serum or cell-free supernatant or even inside the cell.

There is also a means to gain selectivity for RT in assaying a supernatant or sera, by taking advantage of the high ability of the RT from HIV to carry out mismatched DNA synthesis. This refers to the ability of RT to make a poly dG strand upon an poly rA template, and even includes the ability to make a poly dA strand upon a poly rA template. This mismatching is promoted by the lanthanide reagents and can be taken advantage of to help avoid detection of DNA strands made by other nucleic acid polymerases which might happen to be present in the supernatant or sera.

RT assays with a wide variety of metal cations can be conducted by modifying the Potts method (supra) to accommodate the special requirements for solubility imposed by the chemistry of the various elements. Dithiothreitol (DTT) or elevated pH causes immediate precipitation of transition metals; it is therefore appropriate to use, say, the procedure of Temin and Mizutani, Nature 226:1211–1213 (1970) who showed good activity without DTT when assays were run at 0° to 4° C. A buffer pH of 7.3 is tolerated by most of the cations and by the enzyme. Copper cations precipitate in HEPES buffer but not in Tris. Ferrous and ferric cations are insoluble at pH greater than 4.0 and so iron cannot be used in these assays without a "metal buffer" chelator at greatly reduced effective concentrations. Lanthanides precipitate in the presence of dTTP (deoxy thymidine triphosphate) unless pH is greater than 8.2 and cation molarity is equal to or less than 1 millimolar when the molar ratio of cation to dTTP is greater than 1:2.

The $V_{max}$ of an enzyme cannot usually be increased. However, in vitro studies of retroviral reverse transcriptase have demonstrated that RT expends considerable time repeatedly "falling off" its template; see Alford et al, Virology 183:611–619 (1991). An alteration in the enzyme shape which makes RT act more like a conventional high fidelity polymerase by remaining attached to the template until a full transcript is completed would appear to cause the rate of cDNA production to increase sharply. Without wishing to be bound by theory, this may be the mechanism which accounts for the hyperactivation.

This invention is based on the discovery of "amplification", although it will be appreciated that this effect is not necessarily a direct effect on the enzyme itself. It is rather an enhancement of processivity. As will also be appreciated, and readily ratified, by the skilled man, some experimentation may be necessary in order to establish which is the preferred ion for use with the enzyme for which enhanced processivity is required.

The polymerase that is affected may be a retrovirus such as AMV or HIV reverse transcriptase. In particular, for reverse transcriptase (RT), this has applications in turning the relatively insensitive RT assay into a potential diagnostic kit which could be used for screening of blood products for retroviruses such as HIV-1, HIV-2 and HTLV-1. It could also potentially be used to seek evidence of retroviruses (identified and unidentified) in conditions where their presence is suspected but no assay is available. The current concern about "HIV negative AIDS" is one such example. It also has research applications in that for a number of commonly used retroviruses in research (some of which may be used in gene therapy) it is extremely difficult to measure RT and this would be a very useful laboratory tool.

The polymerase chain reaction has wide research and diagnostic applications and a way of enhancing this would be invaluable. The methodology may be able to optimise a variety of aspects of the PCR including enzyme processivity, annealing temperatures, primer binding, etc.

It appears that nucleic acid polymerase and other enzymes have characteristic responses to a range of Group 3 and other ions. In a further aspect of the invention, a plurality (usually at least 3, preferably at least 4 and more preferably at least 5) of ions are used in an assay to identify, from the characteristic "fingerprint" of responses, which of the enzymes is present in a sample.

Suitable test procedures are described herein. Any assay of the invention will often be performed in the presence of a chelating agent and/or a suitable buffer. Examples of such materials are given below.

The basic requirements for the reverse transcription include an absolute requirement for a thioprotectant such as DTT, a preference for an eligo dT primed strand of poly rA as a template, a pH optimum close to pH 8.0, and a requirement for a divalent cation such as $Mn^{2+}$ or $Mg^{2+}$. In this assay, the divalent cation is omitted from the initial "cocktail". Instead, the desired mix of divalent and or trivalent cations, together with any desired chelating agents such as NTA, EDTA, EGTA, or DTPA are made up to ten times the desired final strength in 0.05N HCl, then added to the assay mix only after the RT has been added to the cocktail. In this fashion the selected lanthanide trivalent cation or other selected cation is used to actually start the reaction. When certain divalent cations are used, it is necessary to avoid the use of DTT. In these cases, the reaction must be carried out at 0°–4° C. and not at 37° C. as is usual and the time of the reaction must be doubled.

The "macroassay" assay involves preparation of a cocktail of the reactants including a labelled dTTP. A detergent such as NP-40 is used to inactivate the virus and allow uncoating of the nucleocapsid core which contains up to a hundred copies of RT per viral particle. The treated viral sample is then added to the cocktail to allow synthesis of a radiolabelled thymidine strand upon the poly rA template when the cation is added. This reaction is stopped after 90 minutes by addition of cold 10% TCA, pyrophosphate, and unlabelled eligo dT or tRNA. The TCA precipitate is then poured onto a GF/A glass microfilter and washed extensively with 5% TCA. The labelled, precipitated DNA strands are caught in the filter, while unincorporated nucleotides are washed away. Finally, the filter is dried by washing with ethanol, transferred to a scintillation vial, and counted in scintillant. This method allows only about 30 samples per day. Its advantages are in the precise timing of the reaction and in the expectation that it will be quantitative.

A microassay for RT uses a simpler technique for stopping the reaction and for separating DNA from unincorporated nucleotides. The initial cocktail is essentially identical, but the reactions are run in small volumes in a 96-well plate. After 90 minutes, a replicator or a multichannel pipettor is used to dot 5 µl amounts onto Whatman DE-81 paper (Diethyl aminoethyl or DEAE cellulose). After dotting, the reactions stop when the DE-81 sheet air dries. The DNA adheres to the charged surface of the DE-81 paper, but the unincorporated nucleotides are easily washed off with several rinses of 2×SSC (saline sodium citrate). In these techniques, the paper is finally rinsed with ethanol, dried, cut into 96 small squares, and these are each placed in a scintillation vial for counting.

The inclusion of bovine serum albumin is theoretically useful in order to stabilise the reverse transcriptase and to reduce the impact of any protease present in the sample. However, even when expensively prepared, RNase free BSA is used, it increases variability and actually reduces the maximal RT activity level and so is omitted from this cocktail.

This technique may be used with minimal modification for assays with the Canberra-Packard Matrix[96]. However, when large numbers of samples are to be run, several helpful changes can be made. Principally, the divalent cation is omitted from the initial reaction cocktail, and 0.1 mM EDTA is added. Thus, when the viral sample is added to the cocktail, the reaction does not commence immediately. The EDTA helps in two ways. It ties up any magnesium present in the medium, but it also ties up calcium. This latter manoeuvre is helpful for inhibition of calcium dependent nucleases present in many cells prior to the addition of trivalent cations. Since the affinity of EDTA for calcium (log K=10.7) is much higher than for magnesium (log K= 8.7), the calcium will remain bound even if additional magnesium is added later. Trivalent cations may displace either magnesium or calcium but provide their own protectant effect.

EGTA (Sigma E 4378) provides an even greater differential affinity (log K= 11.0 for Ca, log K= 5.2 for Mg), but its solubility is lower making it more problematic for use in preparing concentrated premixes for the reagents. EGTA can be rendered more soluble by making up the EGTA as its meglumine salt (by adding an equal weight of N-methyl glucamine which has no effect on the RT reaction. However, EGTA is less effective than EDTA for the purposes of this technique which requires tying up magnesium present in the culture medium to prevent premature start of the reaction.

In this tarnion, large numbers of samples can be loaded into wells over several hours without concern for commencing the reaction. RT itself is quite stable at room temperature over this sort of interval, but completed trays can be refrigerated or even frozen in advance of running the actual assay. When all the trays for an assay run are fully assembled, reactions are started by first bringing the tray to 37° C., then adding the cation solution. This technique is particularly helpful when the assay samples are to be loaded from individual tubes in 5 µl quantities. This step can take 45 minutes per assay tray and may involve the transfer of fully infectious virus. The addition of the magnesium can be done by multichannel pipettor and so requires only 2–3 minutes per tray.

The actual assay is done as a continuous "flight" of 20 trays, at five minute intervals, starting each tray by the addition of magnesium. The reaction in each tray is run for 100 minutes. In this fashion, the first tray is completing its 100 minute incubation just after the last (twentieth) tray is started by the addition of magnesium. The reactions are terminated by dotting onto the DE-81 paper for drying. Alternatively, a more precise termination of the reaction can be achieved by using a multichannel pipettor to add 5 µl/well of a stop solution of 1 mM cold dTTP in 250 mM pyrophosphate prior to dotting.

EXAMPLE 1

Cocktail

Each 96 well tray requires 4 ml of RT cocktail. Requirements listed below include amounts for preparing 80 ml of cocktail for a 20 tray assay run. All reagents may be purchased in "molecular biology" grade which is clear of confounding RNase activity.. The cocktail is added to the wells in a quantity of 40 µl. The sample is then added in a 5 µl volume, and finally the divalent cation is added in a 5 µl volume. The concentrations listed are based on this final running volume of 50 µl.

|  |  | Final Conc. |
|---|---|---|
| ddH$_2$O | 78 ml |  |
| Tris HCl<br>Sigma T 7149 | 400 mg |  |
| Tris Base<br>Sigma T 8524 | 300 mg | 50 mM |
| KCl<br>Sigma P-9541 | 560 mg | 75 mM |
| Oligo dT<br>Pharmacia 27-7858-01 (5 A$_{260}$ units =<br>300 µg) | 200 µg | 2 µg/ml |
| Poly rA<br>Pharmacia 27-4110-01 (make and freeze<br>5 mg/ml stock) | 500 µg | 5 µg/ml |
| NP-40 10%<br>Boehringer Mannheim 1332–473,<br>10% solution | 500 µl | 0.05% |
| Dithiothreitol<br>Sigma D9779 | 31 mg | 2 mM |
| EDTA 20 mM solution<br>Sigma E 5134 | 500 µl | 0.1 mM |

The final volume of the cocktail is brought to 80 ml and it is passed through a 0.22µ or 0.45µ filter. Complete cocktail can be made up in large batches and stored frozen at –20° C. in 80 ml aliquots for 20 tray experiments or in 4 ml aliquots for single tray experiments.

Nucleotides

The final reagent for the cocktail is the labelled Thymidine 5' triphosphate (dTTP) and this may be $^3$H labelled ($t^{1/2}$=12.3 years) or $^{32}$P labelled ($t^{1/2}$=14 3 days) or immunologically labelled (e.g. digoxigenin). If a tritiated dTTP is used (e.g. Amersham TRK.576) then it may be convenient to add this to the cocktail before freezing it for storage.

Tritium is a less energetic isotope than $^{32}$P, so that the Canberra-Packard Matrix[96], detects about ⅕th of the counts generated by the same amount of $^{32}$P so that a higher concentration of tritiated nucleotide may be required for some assays where low activity is expected (e.g. when infecting macrophages, rather than T-cells). Some of this loss of sensitivity is made up for by the very low background with tritium (0–5) which is about half of that with $^{32}$P (5–10), this is probably because the very small amount of unincorporated nucleotide remaining in the paper is effectively undetectable when tritium is used.

Tritium is actually preferable when it is expected that some wells will have much higher activities than others since tritium minimises any "spill over" activity. The more energetic β-particles from $^{32}$P can cross into the detector area of neighbouring places in the 96-well grid causing a potential cross-talk of about 0.5% to 1% between wells. Thus, there may be relatively little advantage in using $^{32}$P rather than tritium, particularly in the setting of powerful stimulation by lanthanides.

Because of the generally low background counts achieved by the Canberra Packard 96-matrix relative to most scintillation counters, it is possible to use less radionuclide than is required by other techniques. Background counts vary from machine to machine, but scintillation counter backgrounds of 60–100 both for tritium and for $^{32}$P are common. A final concentration of 2.5 µCi/ml of $^{32}$P-dTTP is entirely adequate. Amersham provides a $^{32}$P-dTTP as 250 µCi in 25 µl at an activity of 400 Ci/mMol and a concentration of 10 mCi/ml (PB 10167). This amount can be added to an 80 ml aliquot prior to use.

The lower efficiency of the Matrix[96] with tritium is entirely made up by the far lower background. Nonetheless, tritium will need to be used at a concentration of 5 to 10 µCi/ml to assure adequate sensitivity for the assay.

Detection of non-radioactive label is according to manufacturer's directions as from Boehringer Mannheim for the digoxigenin based reaction, after blocking non-specific protein binding on the DE-81 paper with nuclease free BSA or non-specific antibody.

Start and stop solutions

The divalent cation for initiating the reaction is set up as a 10–50 mM solution by adding the metal chloride to 12 ml of filtered 0.05 N HCl. The optimal result with low noise is obtained with 10 mM lanthanum and the highest activity is obtained with 10 mM scandium. The optional "stop solution" is made up as 5 mg dTTP (sigma T 8635), and 1.1 gm pyrophosphate (Sigma S 9515) in 12 ml dH$_2$O. This is added in a 5 µl volume to terminate the reaction when a precise stopping time is desired.

Wash Solution

For the washes, 20 ×SSC can be prepared by adding 700 grams of NaCl (Sigma S 3014) and 250 grams of Trisodium Citrate (Sigma C 8532) to 3.5 liters of dH$_2$O and bringing the final volume to 4 liters. This will provide sufficient wash for several hundred plates.

Assay Protocol

1. A sheet of DE-81 (46×57 cm) is cut into six sections (three at 24×15 cm and three at 32×15 cm) and a 96 well pattern is printed on the sheets by a laser printer. The sheets are used as printed with three or four 96-well grid patterns per sheet. At the time of use, individual identifications should be written on each grid in pencil prior to start of the assay.
2. Labelled dTTP is added to cocktail and sequentially labelled 96-well trays (avoid "tissue culture treated" trays) are loaded with 40 µl/well of the complete cocktail. Trays may be frozen and stored in a β-shield box (Sigma S 4144, or Nalgene 6740–1108).
3. Cell free tissue culture supernatants, clear plasma, or recombinant enzyme (1–5 units per well) is added to the wells in 5 µl aliquots. This process can be greatly simplified if the samples can be stored in slim microtubes which can be set up in 96-well format (Biorad 223-9395) then transferred to the cocktail by multi-channel pipettor.
4. The trays are placed in an incubator and brought to 37° C. Forty racks of 96 pipette tips are required for the conduct of the 20 tray assay.
5. At five minute intervals, a tray is removed from the incubator, the reaction commenced by adding 5 µl of the cation solution to each well with a multi-channel pipettor. It is important to mix well by carefully pumping the pipettor upon adding the cation. The tray is returned to the incubator and the next tray brought out for addition of cation.
6. At the end of 100 minutes, all 20 trays should be in the incubator with all the reactions running. The first tray will now be finished its incubation and can be removed from the incubator for dotting.

7. The samples are dotted onto the DE-81 paper in the appropriate grid locations at a volume of 5 μl per dot using a multi-channel pipettor. There will be time for a brief mix with the pipettor before withdrawing the aliquot for dotting. Care must be taken to avoid puncturing or scratching the DE-81 paper with the pipette tips during this step as this may result in some adhesion of unincorporated nucleotides. It is important to use a pipettor with good precision at 5 μl volumes. The BCL 7000 (Boehringer Mannheim) works well and uses rigid pipetted tips (Sigma P 5161) which assure easy alignment of the dots to the grid.

8. As each sheet of three or four 96-well patterns is fully dotted, it may be hung up to dry by puncturing one corner with a partially unbent paper clip to use as a hanger.

9. Once all twenty plates are completed, and all the sheets have dried, they may be washed en masse in a large pyrex dish. The sheets must be cut to include either two or three grids per sheet prior to washing. The washing process is sufficiently efficient as to result in a very low background even when all the sheets are washed together.

10. For each wash the 20 ×SSC is diluted 1:10 with $dH_2O$. One liter of the resulting 2 ×SSC is poured into the dish, submerging the DE-81 sheets. The tray is agitated gently for five minutes and the wash poured out. This is repeated for four washes. A rotating mixer platform can be used.

11. Finally, it is necessary to carry out two washes in 95–100% ethanol for one minute each. This step is required even though no scintillation fluid is used because the DE-81 paper tears when manipulated if it is wet with water. However, once wetted with ethanol, it has much greater wet strength. After pouring off the ethanol, the sheets can be gently lifted from the bath and again hung up to dry with unbent paper clips. A sheet with four grids will be too heavy to hang up without tearing when wet, which is why the sheets must be cut to include only two or three grids prior to washing.

12. Once fully dried, each 96-well pattern can be counted in one minute on the Canberra Packard Matrix[96] machine. The sensitivity of the assay can be increased by using 10 μCi/ml of $^{32}$P-dTTP, and by doubling the aliquot of sample of 10 μl.

EXAMPLE 2

RT activity was compared using various cations. The accompanying FIG. 1 shows, with cations ranked in sequence of ionic radius, HIV-1 reverse transcriptase activity with monovalent (Li) and trivalent (Al, Sc, Lu, Y, Tb, Gd, Ce, La) cations. Assays were run at 34° C. with 2 mM DTT in 150 mM Tris, pH 8.2 except $Al^{3+}$ run in 150 mM HEPES, pH 7.3. For comparison, various divalent cations were run at 0° to 4° C. with no DTT in 150 mM HEPES, pH 7.3, except $Cu^{2+}$ run in 150 mM Tris, pH 7.5. The various complete buffers were made in deionised, metal-free water with 75 mMKCl, poly-rA 5 μg/ml, eligo $dT^{(12-18)}$ 5 μg/ml, peroxide free NP-40 0.05%, and [$^{32}$P]dTTP 5 μCi/ml. The various cocktails were transferred to 96 well plates in volumes of 100 μl/well, and the plates then frozen. Metal solutions were prepared as 250 mM in 0.1N HCl and serial dilutions then made in 0.1N HCl to set up 96 well plates containing the various metals in the various final concentrations. The RT cocktail plates were then thawed and 20 μl of HIV-infected cell free supernatant added to one set of plates while a control set received 20 μl of uninfected cell free supernatant from identical cultures and media; an internal control well for each complete buffer channel received both 10 units of purified MoMuLV RT (Pharmacia) and 20 μl of cell free, uninfected supernatant. Reactions were started by transferring the various metal cation dilutions and $MgCl_2$ dilutions in 8 μl volumes to appropriate locations in HIV, MoMuLV, and control wells for each buffer/DTT/temperature condition using a multi-channel pipettor. 5 μl dot transfers to pre-numbered array locations on DE81 Whatman paper at 2 hours (34° C. plates) or at 4 hours (0° to 4° C. plates) after start of the reaction were dried, washed, cut in squares and β-counted in 5 ml of scintillant. For the results shown in the drawing, the activity from each control well is subtracted from the value for its corresponding assay well (MoMuLV internal controls are not shown). The comparative tests for Cu, Co, Ni, Zn, Mn, Pd and Mg showed maximum RT activity (for Mn), at about 1200. Other results were lower.

In addition, gels were run to demonstrate stereotypical DNA length fragments separated by size. In comparison of Mg, Mn, La, Lu, Y, Tb, Tb+Mg and Sc+ Mg, there were fewer break-points, and more long DNA segments, in channels run with Group 3 elements alone.

EXAMPLE 3

Assays were run to determine the processivity enhancement of Taq polymerase at 70° C. While Mg showed a mean tritium count of c.160, the corresponding counts for Co, Cu, Ni, Mn and La were low, and for Sc, Ce, Nd and Y were respectively approx. 470, 440, 260 and 180.

EXAMPLE 4

Assays were run to determine the processivity effect, using various Group 3, divalent and transition metal ions, on AMV and HIV reverse transcriptases. Each enzyme showed a characteristic pattern of effects, as shown in the Tables 1 through 8 that follow.

TABLE 1

| Lanth/Chel AMV | | | | |
|---|---|---|---|---|
| | Lithium | Strontium | Sc/NTA | Sc/EDTA |
| Buffer | Tris,pH 8.2 | Tris,pH 8.2 | Tris,pH 8.2 | Tris,pH 8.2 |
| DTT | 2 mM | 2 mM | 2 mM | 2 mM |
| Temp. | 34° C. | 34° C. | 34° C. | 34° C. |
| 0.1 mM Me | 48 | 140 | 465 | 89 |
| 0.5 mM Me | 84 | 103 | 1670 | 119 |
| 1.0 mM Me | 105 | 123 | 1792 | 38 |
| 3.0 mM Me | 99 | 151 | 5002 | 39 |
| 0.5 mM Mg/ 1.0 mM Me | 9301 | 9201 | 12324 | 311 |
| 1.0 mM Mg/ 1.0 mM Me | 8464 | 12207 | 13115 | 10216 |
| 3.0 mM Mg/ 1.0 mM Me | 5870 | 12914 | 25281 | 11597 |
| 3.0 mM Mg/ 3.0 mM Me | 10381 | 12174 | 19911 | 13107 |

| | Sc/DTPA | Gd/NTA | Gd/ EDTA | Gd/DTPA (Mgn) |
|---|---|---|---|---|
| Buffer | Tris,pH 8.2 | Tris,pH 8.2 | Tris,pH 8.2 | Tris,pH 8.2 |
| DTT | 2 mM | 2 mM | 2 mM | 2 mM |
| Temp. | 34° C. | 34° C. | 34° C. | 34° C. |
| 0.1 mM Me | 93 | 36 | 73 | 146 |
| 0.5 mM Me | 34 | 49 | 112 | 70 |
| 1.0 mM Me | 20 | 70 | 63 | 98 |
| 3.0 mM Me | 31 | 41 | 33 | 95 |
| 0.5 mM Mg/ 1.0 mM Me | 115 | 6667 | 574 | 11111 |
| 1.0 mM Mg/ 1.0 mM Me | 3791 | 12682 | 9916 | 12178 |
| 3.0 mM Mg/ | 11648 | 6534 | 13213 | 12731 |

TABLE 1-continued

Lanth/Chel AMV

| | | | | |
|---|---|---|---|---|
| 1.0 mM Me | | | | |
| 3.0 mM Mg/ | 13242 | 14721 | 13123 | 12699 |
| 3.0 mM Me | | | | |

| | Gd/DTPA (Sal) | Magnesium | Magnesium | Aluminium |
|---|---|---|---|---|
| Buffer | Tris, pH 8.2 | Tris, pH 8.2 | HEPES, pH 7.3 | HEPES, pH 7.3 |
| DTT | 2 mM | | | |
| Temp. | 34° C. | 34° C. | 34° C. | 34° C. |
| 0.1 mM Me | 85 | 121 | 1600 | 341 |
| 0.5 mM Me | 89 | 514 | 8513 | 3188 |
| 1.0 mM Me | 139 | 1584 | 7446 | 4714 |
| 3.0 mM Me | 187 | 3613 | 10655 | DTPA:81 |
| 0.5 mM Mg/ 1.0 mM Me | 9973 | 2231 | 10955 | 6636 |
| 1.0 mM Mg/ 1.0 mM Me | 12017 | 2228 | 12188 | 10106 |
| 3.0 mM Mg/ 1.0 mM Me | 12534 | 2540 | 12753 | 7245 |
| 3.0 mM Mg/ 3.0 mM Me | 12589 | 5643 | 11529 | DPTA: 13725 |

TABLE 2

Lanth/Chel HIV

| | Lithium | Strontium | Sc/NTA | Sc/EDTA |
|---|---|---|---|---|
| Buffer | Tris, pH 8.2 | Tris, pH 8.2 | Tris, pH 8.2 | Tris, pH 8.2 |
| DTT | 2 mM | 2 mM | 2 mM | 2 mM |
| Temp. | 34° C. | 34° C. | 34° C. | 34° C. |
| 0.1 mM Me | 950 | 698 | 1142 | 705 |
| 0.5 mM Me | 570 | 659 | 1474 | 755 |
| 1.0 mM Me | 504 | 541 | 1045 | 322 |
| 3.0 mM Me | 433 | 588 | 916 | 205 |
| 0.5 mM Mg/ 1.0 mM Me | 15920 | 14418 | 8908 | 7339 |
| 1.0 mM Mg/ 1.0 mM Me | 15944 | 15775 | 12983 | 12698 |
| 3.0 mM Mg/ 1.0 mM Me | 15651 | 15172 | 12268 | 13925 |
| 3.0 mM Mg/ 3.0 mM Me | 15115 | 14441 | 9185 | 13619 |

| | Sc/DTPA | Gd/NTA | Gd/EDTA | Gd/DTPA (Mgn) |
|---|---|---|---|---|
| Buffer | Tris, pH 8.2 | Tris, pH 8.2 | Tris, pH 8.2 | Tris, pH 8.2 |
| DTT | 2 mM | 2 mM | 2 mM | 2 mM |
| Temp. | 34° C. | 34° C. | 34° C. | 34° C. |
| 0.1 mM Me | 550 | 843 | 708 | 892 |
| 0.5 mM Me | 286 | 837 | 599 | 633 |
| 1.0 mM Me | 206 | 543 | 651 | 789 |
| 3.0 mM Me | 157 | 390 | 182 | 699 |
| 0.5 mM Mg/ 1.0 mM Me | 564 | 8764 | 7849 | 13829 |
| 1.0 mM Mg/ 1.0 mM Me | 10325 | 9562 | 14319 | 12074 |
| 3.0 mM Mg/ 1.0 mM Me | 12149 | 8792 | 14817 | 13180 |
| 3.0 mM Mg/ 3.0 mM Me | 12574 | 13234 | 13379 | 12748 |

| | Gd/DTPA (Sal) | Mg, no DTT | Mg, bufferB | Aluminium |
|---|---|---|---|---|
| Buffer | Tris, pH 8.2 | Tris, pH 8.2 | HEPES, pH 7.3 | HEPES, pH 7.3 |
| DTT | 2 mM | | | |
| Temp. | 34° C. | 34° C. | 34° C. | 34° C. |
| 0.1 mM Me | 659 | 14124 | 14469 | 503 |
| 0.5 mM Me | 938 | 14216 | 15109 | 1496 |
| 1.0 mM Me | 572 | 13661 | 11838 | 1356 |
| 3.0 mM Me | 935 | 13294 | 11673 | DTPA:67 |
| 0.5 mM Mg/ 1.0 mM Me | 14066 | 14495 | 16001 | 2213 |
| 1.0 mM Mg/ 1.0 mM Me | 13555 | 13774 | 12351 | 2587 |
| 3.0 mM Mg/ 1.0 mM Me | 13668 | 12726 | 8922 | 8227 |
| 3.0 mM Mg/ 3.0 mM Me | 13804 | 15022 | 13493 | DPTA: 13868 |

TABLE 3

Lanth/Chel Control (no RT)

| | Lithium | Strontium | Sc/NTA | Sc/EDTA |
|---|---|---|---|---|
| Buffer | Tris, pH 8.2 | Tris, pH 8.2 | Tris, pH 8.2 | Tris, pH 8.2 |
| DTT | 2 mM | 2 mM | 2 mM | 2 mM |
| Temp. | 34° C. | 34° C. | 34° C. | 34° C. |
| 0.1 mM Me | 3 | 10 | 4 | 8 |
| 0.5 mM Me | 7 | 8 | 3 | 4 |
| 1.0 mM Me | 3 | 11 | 12 | 8 |
| 3.0 mM Me | 8 | 9 | 96 | 7 |
| 0.5 mM Mg/ 1.0 mM Me | 2 | 7 | 13 | 4 |
| 1.0 mM Mg/ 1.0 mM Me | 8 | 3 | 10 | 5 |
| 3.0 mM Mg/ 1.0 mM Me | 3 | 6 | 16 | 2 |
| 3.0 mM Mg/ 3.0 mM Me | 57 | 11 | 49 | 1 |

| | Sc/DTPA | Gd/NTA | Gd/EDTA | Gd/DTPA (Mgn) |
|---|---|---|---|---|
| Buffer | Tris, pH 8.2 | Tris, pH 8.2 | Tris, pH 8.2 | Tris, pH 8.2 |
| DTT | 2 mM | 2 mM | 2 mM | 2 mM |
| Temp. | 34° C. | 34° C. | 34° C. | 34° C. |
| 0.1 mM Me | 8 | 6 | 6 | 3 |
| 0.5 mM Me | 11 | 9 | 4 | 4 |
| 1.0 mM Me | 9 | 11 | 6 | 14 |
| 3.0 mM Me | 9 | 6 | 8 | 3 |
| 0.5 mM Mg/ 1.0 mM Me | 5 | 3 | 27 | 6 |
| 1.0 mM Mg/ 1.0 mm Me | 3 | 2 | 6 | 5 |
| 3.0 mM Mg/ 1.0 mM Me | 13 | 3 | 7 | 5 |
| 3.0 mM Mg/ 3.0 mM Me | 3 | 6 | 7 | 3 |

| | Gd/DTPA (Sal) | Mg, no DTT | Mg, bufferB | Aluminium |
|---|---|---|---|---|
| Buffer | Tris, pH 8.2 | Tris, pH 8.2 | HEPES, pH 7.3 | HEPES, pH 7.3 |
| DTT | 2 mM | | | |
| Temp. | 34° C. | 34° C. | 34° C. | 34° C. |
| 0.1 mM Me | 4 | 6 | 28 | 125 |
| 0.5 mM Me | 1 | 7 | 41 | 1416 |
| 1.0 mM Me | 10 | 13 | 22 | 856 |
| 3.0 mM Me | 6 | 9 | 17 | DTPA:16 |
| 0.5 mM Mg/ 1.0 mM Me | 7 | 5 | 31 | 1035 |
| 1.0 mM Mg/ 1.0 mM Me | 7 | 14 | 41 | 2509 |
| 3.0 mM Mg/ 1.0 mM Me | 8 | 1 | 24 | 2124 |
| 3.0 mM Mg/ 3.0 mM Me | 0 | 3 | 13 | DPTA:29 |

TABLE 4

Transition Metals/AMV

|  | Copper | Mg/buffer C | Magnesium | Nickel |
|---|---|---|---|---|
| Buffer | Tris, pH 7.5 | Tris, pH 7.5 | HEPES, pH 7.3 | HEPES, pH 7.3 |
| DTT |  |  |  |  |
| Temp. | 0–4° C. | 0–4° C. | 0–4° C. | 0–4° C. |
| 0.1 mM Me | 16 | 253 | 146 | 440 |
| 0.5 mM Me | 32 | 1830 | 727 | 1221 |
| 1.0 mM Me | 12 | 2450 | 1312 | 1364 |
| 3.0 mM Me | 23 | 6485 | 3800 | 1864 |
| 0.5 mM Mg/ 1.0 mM Me | 36 | 3233 | 2209 | 2861 |
| 1.0 mM Mg/ 1.0 mM Me | 52 | 3890 | 2175 | 3478 |
| 3.0 mM Mg/ 1.0 mM Me | 145 | 5025 | 3911 | 5537 |
| 3.0 mM Mg/ 3.0 mM Me | 107 | 7650 | 5940 | 5397 |

|  | Zinc | Cobalt | Manganese | Palladium |
|---|---|---|---|---|
| Buffer | HEPES, pH 7.3 | HEPES, pH 7.3 | HEPES, pH 7.3 | HEPES, pH 7.3 |
| DTT |  |  |  |  |
| Temp. | 0–4° C. | 0–4° C. | 0–4° C. | 0–4° C. |
| 0.1 mM Me | 6165 | 9678 | 15176 | 140 |
| 0.5 mM Me | 5674 | 13103 | 14190 | 142 |
| 1.0 mM Me | 4085 | 5241 | 13124 | 108 |
| 3.0 mM Me | 6237 | 11431 | 10191 | 57 |
| 0.5 mM Mg/ 1.0 mM Me | 3612 | 12752 | 13096 | 87 |
| 1.0 mM Mg/ 1.0 mM Me | 2341 | 12572 | 13649 | 80 |
| 3.0 mM Mg/ 1.0 mM Me | 1897 | 13239 | 13037 | 111 |
| 3.0 mM Mg/ 3.0 mM Me | 2215 | 13527 | 13006 | 78 |

|  | Tin | Lanth/O | Lanth/N | Mn DPDP |
|---|---|---|---|---|
| Buffer | HEPES, pH 7.3 | HEPES, pH 7.3 | HEPES, pH 7.3 | HEPES, pH 7.3 |
| DTT |  |  |  |  |
| Temp. | 0–4° C. | 0–4° C. | 0–4° C. | 0–4° C. |
| 0.1 mM Me | 45 | 235 | 649 | 643 |
| 0.5 mM Me | 70 | 4875 | 4446 | 339 |
| 1.0 mM Me | 126 | 3042 | 4617 | 656 |
| 3.0 mM Me | 498 | DTPA:48 | DTPA:50 | 546 |
| 0.5 mM Mg/ 1.0 mM Me | 343 | 2806 | 4057 | 4930 |
| 1.0 mM Mg/ 1.0 mM Me | 440 | 3002 | 2654 | 5638 |
| 3.0 mM Mg/ 1.0 mM Me | 1034 | 25569 | 2085 | 9768 |
| 3.0 mM Mg/ 3.0 mM Me | 1303 | DTPA:2396 | DTPA:1477 | 11014 |

TABLE 5

Transition Metals/HIV

|  | Copper | Mg/C | Magnesium | Nickel |
|---|---|---|---|---|
| Buffer | Tris, pH 7.5 | Tris, pH 7.5 | HEPES, pH 7.3 | HEPES, pH 7.3 |
| DTT |  |  |  |  |
| Temp. | 0–4° C. | 0–4° C. | 0–4° C. | 0–4° C. |
| 0.1 mM Me | 1873 | 10484 | 11076 | 10934 |
| 0.5 mM Me | 4604 | 12691 | 12529 | 11966 |
| 1.0 mM Me | 3928 | 11610 | 13288 | 12353 |
| 3.0 mM Me | 9926 | 12368 | 12739 | 11656 |
| 0.5 mM Mg/ 1.0 mM Me | 13237 | 12905 | 10821 | 11871 |
| 1.0 mM Mg/ 1.0 mM Me | 15182 | 13220 | 12426 | 11592 |
| 1.0 mM Mg/ 3.0 mM Me | 14703 | 15028 | 11335 | 12210 |
| 3.0 mM Mg/ 3.0 mM Me | 14147 | 13708 | 12928 | 12655 |

|  | Zinc | Cobalt | Manganese | Palladium |
|---|---|---|---|---|
| Buffer | HEPES, pH 7.3 | HEPES, pH 7.3 | HEPES, pH 7.3 | HEPES, pH 7.3 |
| DTT |  |  |  |  |
| Temp. | 0–4° C. | 0–4° C. | 0–4° C. | 0–4° C. |
| 0.1 mM Me | 10105 | 13517 | 12707 | 195 |
| 0.5 mM Me | 11994 | 12679 | 13167 | 127 |
| 1.0 mM Me | 11349 | 11607 | 11856 | 148 |
| 3.0 mM Me | 9793 | 11104 | 11041 | 107 |
| 0.5 mM Mg/ 1.0 mM Me | 9489 | 10830 | 11660 | 1070 |
| 1.0 mM Mg/ 1.0 mM Me | 9795 | 11512 | 11660 | 2587 |
| 3.0 mM Mg/ 1.0 mM Me | 10155 | 10295 | 12352 | 2727 |
| 3.0 mM Mg/ 3.0 mM Me | 10988 | 11931 | 13768 | 1105 |

|  | Tin | Lanth/O | Lanth/N | Mn DPDP |
|---|---|---|---|---|
| Buffer | HEPES, pH 7.3 | HEPES, pH 7.3 | HEPES, pH 7.3 | HEPES, pH 7.3 |
| DTT |  |  |  |  |
| Temp. | 0–4° C. | 0–4° C. | 0–4° C. | 0–4° C. |
| 0.1 mM Me | 644 | 127 | 124 | 10422 |
| 0.5 mM Me | 965 | 129 | 140 | 12739 |
| 1.0 mM Me | 1028 | 50 | 151 | 11662 |
| 3.0 mM Me | 4100 | DTPA:46 | DTPA:47 | 12844 |
| 0.5 mM Mg/ 1.0 mM Me | 10987 | 148 | 217 | 13731 |
| 1.0 mM Mg/ 1.0 mm Me | 9090 | 99 | 268 | 13938 |
| 3.0 mM Mg/ 1.0 mM Me | 13863 | 377 | 441 | 13383 |
| 3.0 mM Mg/ 3.0 mM Me | 14042 | DTPA: 12294 | DTPA: 15409 | 14588 |

TABLE 6

Transition Metals/Control (no RT)

|  | Copper | Mg/C | Magnesium | Nickel |
|---|---|---|---|---|
| Buffer | Tris, pH 7.5 | Tris, pH 7.5 | HEPES, pH 7.3 | HEPES, pH 7.3 |
| DTT |  |  |  |  |
| Temp. | 0–4° C. | 0–4° C. | 0–4° C. | 0–4° C. |
| 0.1 mM Me | 5 | 8 | 17 | 26 |
| 0.5 mM Me | 9 | 5 | 16 | 13 |
| 1.0 mM Me | 13 | 8 | 15 | 13 |
| 3.0 mM Me | 12 | 4 | 15 | 14 |
| 0.5 mM Mg/ 1.0 mM Me | 8 | 5 | 29 | 16 |
| 1.0 mM Mg/ 1.0 mM Me | 13 | 4 | 18 | 10 |
| 3.0 mM Mg/ 1.0 mM Me | 13 | 9 | 10 | 14 |
| 3.0 mM Mg/ 3.0 mM Me | 2 | 7 | 14 | 10 |

|  | Zinc | Cobalt | Manganese | Palladium |
|---|---|---|---|---|
| Buffer | HEPES, pH 7.3 | HEPES, pH 7.3 | HEPES, pH 7.3 | HEPES, pH 7.3 |
| DTT |  |  |  |  |
| Temp. | 0–4° C. | 0–4° C. | 0–4° C. | 0–4° C. |
| 0.1 mM Me | 15 | 12 | 17 | 131 |
| 0.5 mM Me | 12 | 16 | 12 | 172 |

TABLE 6-continued

Transition Metals/Control (no RT)

| | | | | |
|---|---|---|---|---|
| 1.0 mM Me | 20 | 8 | 7 | 170 |
| 3.0 mM Me | 53 | 18 | 11 | 94 |
| 0.5 mM Mg/ 1.0 mM Me | 17 | 21 | 22 | 107 |
| 1.0 mM Mg/ 1.0 mM Me | 9 | 17 | 12 | 133 |
| 3.0 mM Mg/ 1.0 mM Me | 17 | 15 | 13 | 109 |
| 3.0 mM Mg/ 3.0 mM Me | 12 | 15 | 13 | 68 |

| | Tin | Lanth/O | Lanth/N | Mn DPDP |
|---|---|---|---|---|
| Buffer | HEPES, pH 7.3 | HEPES, pH 7.3 | HEPES, pH 7.3 | HEPES, pH 7.3 |
| DTT | | | | |
| Temp. | 0–4° C. | 0–4° C. | 0–4° C. | 0–4° C. |
| 0.1 mM Me | 70 | 37 | 11 | 13 |
| 0.5 mM Me | 186 | 21 | 12 | 5 |
| 1.0 mM Me | 781 | 60 | 11 | 11 |
| 3.0 mM Me | 7048 | 25 | 22 | 6 |
| 0.5 mM Mg/ 1.0 mM Me | 526 | 27 | 4 | 9 |
| 1.0 mM Mg/ 1.0 mM Me | 272 | 25 | 5 | 17 |
| 3.0 mM Mg/ 1.0 mM Me | 376 | 116 | 11 | 10 |
| 3.0 mM Mg/ 3.0 mM Me | 2285 | 28 | 17 | 8 |

TABLE 7

HIV1 RT Assay

| | 1: A–H Cerium | 2: A–H Gadolinium | 3: A–H Lanthanum | 4: A–H Lutetium |
|---|---|---|---|---|
| Buffer | HEPES, pH 7.3 | HEPES, pH 7.3 | HEPES, pH 7.3 | HEPES, pH 7.3 |
| DTT | 2 mM | 2 mM | 2 mM | 2 mM |
| Temp. | 34° C. | 34° C. | 34° C. | 34° C. |
| 0.1 mM Me | 8262 | 2136 | 6238 | 3612 |
| 0.5 mM Me | 106210 | 26242 | 65860 | 5145 |
| 1.0 mM Me | 104630 | 16286 | 90826 | 18869 |
| 1.0 mM Mg/ 1.0 mM Me | 69766 | 10438 | 22320 | 13428 |
| 2.0 mM Mg/ 1.0 mM Me | 58140 | 5791 | 12770 | 8478 |
| 4.0 mM Mg/ 1.0 mM Me | 65915 | 11971 | 15978 | 5205 |
| 4.0 mM Mg/ RT/ 1.0 mM Me | 23144 | 24791 | 2016 | 6305 |
| RT(MMLV)/ 1.0 mM Me | 19761 | 72873 | 4695 | 6975 |

| | 5: A–H Scandium | 6: A–H Terbium | 7: A–H Yttrium | 8: A–H Lithium |
|---|---|---|---|---|
| Buffer | HEPES, pH 7.3 | HEPES, pH 7.3 | HEPES, pH 7.3 | HEPES, pH 7.3 |
| DTT | 2 mM | 2 mM | 2 mM | 2 mM |
| Temp. | 34° C. | 34° C. | 34° C. | 34° C. |
| 0.1 mM Me | 22176 | 2254 | 1391 | 1542 |
| 0.5 mM Me | 44624 | 11548 | 27490 | 756 |
| 1.0 mM Me | 74940 | 86040 | 17155 | 870 |
| 1.0 mM Mg/ 1.0 mM Me | 75893 | 63210 | 26125 | 5147 |
| 2.0 mM Mg/ 1.0 mM Me | 58110 | 49372 | 9034 | 10437 |
| 4.0 mM Mg/ 1.0 mM Me | 46192 | 42936 | 47836 | 11396 |
| 4.0 mM Mg/ RT/ 1.0 mM Me | 100640 | 109930 | 31248 | 64115 |
| RT(MMLV)/ 1.0 mM Me | 125380 | 64115 | 55995 | 1059 |

| | 9: A–H Strontium | 10: A–H Magnesium | 11: A–H Aluminium | 12: A–H Cobalt |
|---|---|---|---|---|
| Buffer | HEPES, pH 7.3 | HEPES, pH 7.3 | Tris, pH 8.2 | Tris, pH 8.2 |
| DTT | 2 mM | (2 mM) | 2 mM | |
| Temp. | 34° C. | 34° C. | 34° C. | 34° C. |
| 0.1 mM Me | 935 | 1381 | 8763 | 2812 |
| 0.5 mM Me | 817 | 3374 | 5003 | 3972 |
| 1.0 mM Me | 825 | 6813 | 8658 | 3091 |
| 1.0 mM Mg/ 1.0 mM Me | 5209 | 10169 | 26837 | 3612 |
| 2.0 mM Mg/ 1.0 mM Me | 9923 | 12941 | 31311 | 1408 |
| 4.0 mM Mg/ 1.0 mM Me | 10895 | 10274 | 15328 | 3400 |
| 4.0 mM Mg/ RT/ 1.0 mM Me | 86893 | 86573 | 47952 | 76980 |
| RT(MMLV)/ 1.0 mM Me | 1020 | 81333 | 11294 | 73060 |

TABLE 8

HIV1 RT Assay

| | 1: A'–F' Copper | 2: A'–F' Cobalt | 3: A'–F' Manganese | 4: A'–F' Nickel |
|---|---|---|---|---|
| Buffer | Tris, pH 7.5 | Tris, pH 8.2 | Tris, pH 8.2 | Tris, pH 8.2 |
| DTT | | | | |
| Temp. | 0–4° C. | 0–4° C. | 0–4° C. | 0–4° C. |
| 0.1 mM Me | 616 | 997 | 1284 | 607 |
| 0.5 mM Me | 659 | 1671 | 617 | 596 |
| 1.0 mM Me | 2615 | 1673 | 571 | 699 |
| 1.0 mM Mg/ 1.0 mM Me | 609 | 2160 | 541 | 2204 |
| 2.0 mM Mg/ 1.0 mM Me | 3977 | 2466 | 414 | 2743 |
| 4.0 mM Mg/ 1.0 mM Me | 4813 | 2481 | 191 | 2591 |
| 4.0 mM Mg/ RT/ 1.0 mM Me | 3661 | 72986 | 102020 | 47616 |
| RT(MMLV)/ 1.0 mM Me | 243 | 11431 | 89753 | 398 |

| | 5: A'–F' Palladium | 6: A'–F' Ruthenium | 7: A'–F' Zinc | 8: A'–F' Magnesium |
|---|---|---|---|---|
| Buffer | Tris, pH 8.2 | Tris, pH 8.2 | Tris, pH 8.2 | Tris, pH 8.2 |
| DTT | | | | |
| Temp. | 0–4° C. | 0–4° C. | 0–4° C. | 0–4° C. |
| 0.1 mM Me | 461 | 405 | 394 | 714 |
| 0.5 mM Me | 482 | 490 | 297 | 1275 |
| 1.0 mM Me | 527 | 448 | 277 | 2125 |
| 1.0 mM Mg/ 1.0 mM Me | 1630 | 1184 | 363 | 2506 |
| 2.0 mM Mg/ 1.0 mM Me | 1825 | 367 | 356 | 2354 |
| 4.0 mM Mg/ 1.0 mM Me | 1868 | 478 | 350 | 2616 |
| 4.0 mM Mg/ RT/ 1.0 mM Me | 22553 | 10501 | 445 | 83386 |
| RT(MMLV)/ 1.0 mM Me | 189 | 212 | 265 | 68806 |

| | 9: A'–F' Magnesium | 10: A'–F' Blank | 11: A'–F' Sera | 12: A'–F' Blank |
|---|---|---|---|---|
| Buffer | Tris, pH 7.5 | | HEPES, | |

TABLE 8-continued

HIV1 RT Assay

| DTT Temp. | pH 7.3 | | | |
|---|---|---|---|---|
| | 0–4° C. | 0–4° C. | 0–4° C. | 0–4° C. |
| 0.1 mM Me | 782 | 60 | 132 | 58 |
| 0.5 mM Me | 2582 | 50 | 799 | 49 |
| 1.0 mM Me | 2596 | 54 | 186 | 60 |
| 1.0 mM Mg/ 1.0 mM Me | 3235 | 66 | 178 | 51 |
| 2.0 mM Mg/ 1.0 mM Me | 3229 | 64 | 139 | 79 |
| 4.0 mM Mg/ 1.0 mM Me | 3709 | 79 | 172 | 61 |
| 4.0 mM Mg/ RT/ 1.0 mM Me | 48612 | 76 | 188 | 61 |
| RT(MMLV)/ 1.0 mM Me | 39563 | 107 | 195 | 77,59,68,77 |

We claim:

1. A kit of two or more containers packaged together, the contents comprising an IUPAC Group 3 ion, or a salt thereof, wherein said Group 3 ion is selected from the group consisting of scandium ion and lanthanum ion, and at least one reagent selected from the group consisting of:

(a) a nucleic add polymerase, (b) a template, and (c) a buffer solution having a pH that is substantially the optimum for the polymerase activity of said nucleic acid polymerase.

2. A kit according to claim 1, wherein the polymerase is selected from the group consisting of DNA polymerase, AMV reverse transcriptase, and HIV reverse transcriptase.

3. The kit, according to claim 1, further comprising nitriloacetic acid (NTA).

4. The kit, according to claim 1, wherein said buffer has a pH of about 8.0.

5. A method for increasing the rate of processivity of a nucleic acid polymerase, said method comprising contacting a solution comprising said polymerase with an IUPAC Group 3 ion, or a salt thereof, and a nucleic acid template, wherein said Group 3 ion is selected from the group consisting of scandium ion and lanthanum ion, wherein a complementary nucleic acid is produced from said nucleic acid template.

6. The method, according to claim 5, wherein said polymerase is selected from the group consisting of DNA polymerase, AMV reverse transcriptase, and HIV reverse transcriptase.

7. The method, according to claim 5, wherein said polymerase solution is contacted with said IUPAC Group 3 ion, or a salt thereof, in a mixture comprising nitrilotriacetic acid (NTA).

8. The method according to claim 5, wherein said Group 3 ion inhibits the nucleate activity of nuclease enzymes that may be present in said solution.

9. The method, according to claim 5, wherein said complementary nucleic acid is detected in an assay conducted in vitro on a sample suspected of containing said polymerase or a template therefor.

* * * * *

UNITED STATES PATENT AND TRADEMARK OFFICE
CERTIFICATE OF CORRECTION

PATENT NO. : 5,554,498

DATED : September 10, 1996

INVENTOR(S) : Aaron G. Filler and Andrew M. L. Lever

It is certified that error appears in the above-indentified patent and that said Letters Patent is hereby corrected as shown below:

Column 9, Line 8: "activity.." should read --activity.--
Column 9, Line 41: "= p" should read --$^{32}$P--.
Column 9, Line 41: "14 3 days" should read --14.3 days--.
Column 11, Line 56: "eligo dT$^{(12-18)}$" should read --oligo dT$^{(12-18)}$--.

In the claims,

Column 19, Line 27: "add" should read --acid--.
Column 20, Line 25: "nucleate" should read --nuclease--.

Signed and Sealed this

Fourth Day of February, 1997

BRUCE LEHMAN

Attest:

*Attesting Officer*         *Commissioner of Patents and Trademarks*